US008158583B2

(12) United States Patent
Knudsen et al.

(10) Patent No.: US 8,158,583 B2
(45) Date of Patent: Apr. 17, 2012

(54) SOLUBLE PHARMACEUTICAL COMPOSITIONS FOR PARENTERAL ADMINISTRATION COMPRISING A GLP-1 PEPTIDE AND AN INSULIN PEPTIDE OF SHORT TIME ACTION FOR TREATMENT OF DIABETES AND BULIMIA

(75) Inventors: Liselotte Bjerre Knudsen, Kalundborg (DK); Kristian Tage Hansen, Slangerup (DK); Dorthe Kot Engelund, Holte (DK); Svend Ludvigsen, Lynge (DK); Lars Hansen, Frederiksberg (DK); Claude Bonde, Lyngby (DK); Ejvind Jensen, Birkerød (DK); Tine Elisabeth Gottschalk Bøving, Lyngby (DK); Morten Schlein, København (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/464,444

(22) Filed: May 12, 2009

(65) Prior Publication Data

US 2009/0286716 A1    Nov. 19, 2009

Related U.S. Application Data

(63) Continuation of application No. 11/417,562, filed on May 3, 2006, now abandoned, which is a continuation of application No. PCT/DK2004/000788, filed on Nov. 12, 2004.

(60) Provisional application No. 60/519,590, filed on Nov. 13, 2003.

(30) Foreign Application Priority Data

Nov. 13, 2003 (DK) .................................. 2003 01689

(51) Int. Cl.
*A61K 38/26* (2006.01)
*A61K 38/28* (2006.01)
(52) U.S. Cl. ........... 514/11.7; 514/5.9; 514/6.3; 514/6.8
(58) Field of Classification Search .................. None
See application file for complete search history.

(56) References Cited

U.S. PATENT DOCUMENTS

| | | | |
|---|---|---|---|
| 5,216,126 A | 6/1993 | Cox et al. | |
| 5,514,646 A | 5/1996 | Chance | |
| 5,618,913 A | 4/1997 | Brange et al. | |
| 6,251,856 B1 | 6/2001 | Markussen et al. | |
| 6,458,924 B2 | 10/2002 | Knudsen et al. | |
| 2003/0224983 A1 | 12/2003 | Nielsen | |

FOREIGN PATENT DOCUMENTS

| | | |
|---|---|---|
| EP | 0383472 | 8/1990 |
| JP | 2-264798 | 10/1990 |
| JP | 2000-500505 | 1/2000 |
| JP | 2000-517308 | 12/2000 |
| JP | 2002-508742 | 3/2002 |
| JP | 2003-503356 | 1/2003 |
| JP | 2003-505347 | 2/2003 |
| JP | 2003-519664 | 6/2003 |
| WO | WO98/08871 | 3/1998 |
| WO | WO 98/08871 | 3/1998 |
| WO | WO 98/08872 | 3/1998 |
| WO | WO 98/30231 | 7/1998 |
| WO | WO99/43706 | 9/1999 |
| WO | WO 01/00223 | 1/2001 |
| WO | WO01/00223 | 1/2001 |
| WO | WO 01/04156 | 1/2001 |
| WO | WO 01/51071 | 7/2001 |
| WO | WO03/020201 | 3/2003 |

OTHER PUBLICATIONS

Meier, J. et al., J. Clin. Encodrinol. Metab., 2003, vol. 88, Part 6, pp. 2719-2725.
Mickle et al., Med. Clin. North Am., 2000, vol. 84(3), pp. 597-607.
Pillai, O. et al., Journal of Controlled Release, 2003, vol. 89, pp. 127-140.
Raskin, P. et al., Diabetes Care, 2003, vol. 26, Part 9, pp. 2598-2603.
Verploegen et al., FEBS Letters 405, 1997, pp. 237-240.
European Medicines Agency, Evaluation of Medicines for Human Use, Assessment Report for Victoza®, 2009, Doc. Ref.: EMEA/379172/2009.

*Primary Examiner* — Gyan Chandra
(74) *Attorney, Agent, or Firm* — Teresa Chen

(57) ABSTRACT

Pharmaceutical composition for parenteral administration comprising a meal related insulin peptide and an insulinotropic peptide.

36 Claims, 9 Drawing Sheets

SEQUENCE LISTING

```
<160> NUMBER OF SEQ ID NOS: 3

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 39
<212> TYPE: PRT
<213> ORGANISM: GILA MONSTER
<220> FEATURE:
```

```
<221> NAME/KEY: MISC_FEATURE
<222> LOCATION: (39)..(39)
<223> OTHER INFORMATION: Serine at position 39 is amidated

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 44
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (44)..(44)
<223> OTHER INFORMATION: Lysine at position 44 is amidated

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40
```

SOLUBLE PHARMACEUTICAL COMPOSITIONS FOR PARENTERAL ADMINISTRATION COMPRISING A GLP-1 PEPTIDE AND AN INSULIN PEPTIDE OF SHORT TIME ACTION FOR TREATMENT OF DIABETES AND BULIMIA

CROSS REFERENCE TO RELATED APPLICATIONS

This application is a continuation of U.S. patent application Ser. No. 11/417,562, filed May 3, 2006, which is a continuation of International Application serial no. PCT/DK2004/000788 filed Nov. 12, 2004 and claims priority from Danish Application serial no. PA 2003 01689 filed Nov. 13, 2003 and of U.S. provisional application Ser. No. 60/519,590 filed on Nov. 13, 2003.

FIELD OF THE INVENTION

The present invention relates to the field of pharmaceutical compositions. More specifically the invention pertains to pharmaceutical compositions comprising two different pharmaceutically active peptides.

BACKGROUND OF THE INVENTION

Diabetes mellitus is a metabolic disorder in which the ability to utilize glucose is partly or completely lost. About 5% of all people suffer from diabetes and the disorder approaches epidemic proportions. Since the introduction of insulin in the 1920's, continuous efforts have been made to improve the treatment of diabetes mellitus. Since people suffering from diabetes are subject to chronic treatment over several decades, there is a major need for safe, convenient and life quality improving insulin formulations.

In the treatment of diabetes mellitus, many varieties of insulin formulations have been suggested and used, such as regular insulin, isophane insulin (designated NPH), insulin zinc suspensions (such as Semilente®, Lente®, and Ultralente®), and biphasic isophane insulin. Some of the commercial available insulin formulations are characterized by a fast onset of action and other formulations have a relatively slow onset but show a more or less prolonged action. Fast-acting insulin formulations are usually solutions of insulin, while retarded acting insulin formulations can be suspensions containing insulin in crystalline and/or amorphous form precipitated by addition of zinc salts alone or by addition of protamine or by a combination of both.

Normally, insulin formulations are administered by subcutaneous injection. What is important for the patient is the action profile of the insulin formulation which is the action of insulin on the glucose metabolism as a function of the time from the injection. In this profile, inter alia, the time for the onset, the maximum value, and the total duration of action are important. A variety of insulin formulations with different action profiles are desired and requested by the patients.

Human insulin consists of two polypeptide chains, the so-called A and B chains which contain 21 and 30 amino acid residues, respectively. The A and B chains are interconnected by two cystine disulphide bridges. Insulin from most other species has a similar construction, but may not contain the same amino acid residues at the same positions. Within the last decade a number of human insulin analogues have been developed. They are designed for particular profiles of action, i.e. fast acting or prolonged action.

Another peptide expected to become very important in the treatment of diabetes is glucagon-like peptide-1 (GLP-1). Human GLP-1 is a 37 amino acid residue peptide originating from preproglucagon which is synthesized i.a. in the L-cells in the distal ileum, in the pancreas and in the brain. GLP-1 is an important gut hormone with regulatory function in glucose metabolism and gastrointestinal secretion and metabolism. GLP-1 stimulates insulin secretion in a glucose-dependant manner, stimulates insulin biosynthesis, promotes beta cell rescue, decreases glucagon secretion, gastric emptying and food intake. A simple system is used to describe fragments and analogues of this peptide. Thus, for example, $Gly^8$-GLP-1(7-37) designates an analogue of GLP-1(7-37) formally derived from GLP-1(7-37) by substituting the naturally occurring amino acid residue in position 8 (Ala) by Gly. Similarly, $Lys^{34}(N^\epsilon$-tetradecanoyl)-GLP-1(7-37) designates GLP-1(7-37) wherein the amino group of the Lys residue in position 34 has been tetradecanoylated. PCT publications WO 98/08871 and WO 99/43706 disclose stable derivatives of GLP-1 analogues, which have a lipophilic substituent. These stable derivatives of GLP-1 analogues have a protracted profile of action compared to the corresponding GLP-1 analogues.

As the type 2 diabetes population is rapidly increasing in the world, there is a much larger need for simpler administration of more effective drugs. The combined effects of GLP-1 are expected to give very effective and safe lowering of blood glucose. However, some patients may benefit from an extra small dose of insulin with the main meals. A combination formulation comprising an insulin peptide and a GLP-1 peptide, may with a fixed ratio of the two pharmaceuticals, be a very efficacious treatment as well as one requiring less injections when administered to the same patient. Because only a low dose of insulin is given with the meal and the GLP-1 counterpart of the formulation controls glucose for the rest of the day and night, and since GLP-1 does not lead to hypoglycemia it may also be a very safe treatment.

Thus, there is a big need for stable pharmaceutical compositions comprising meal-related insulin and a GLP-1 peptide in one combined formulation.

SUMMARY OF THE INVENTION

Figure 1:
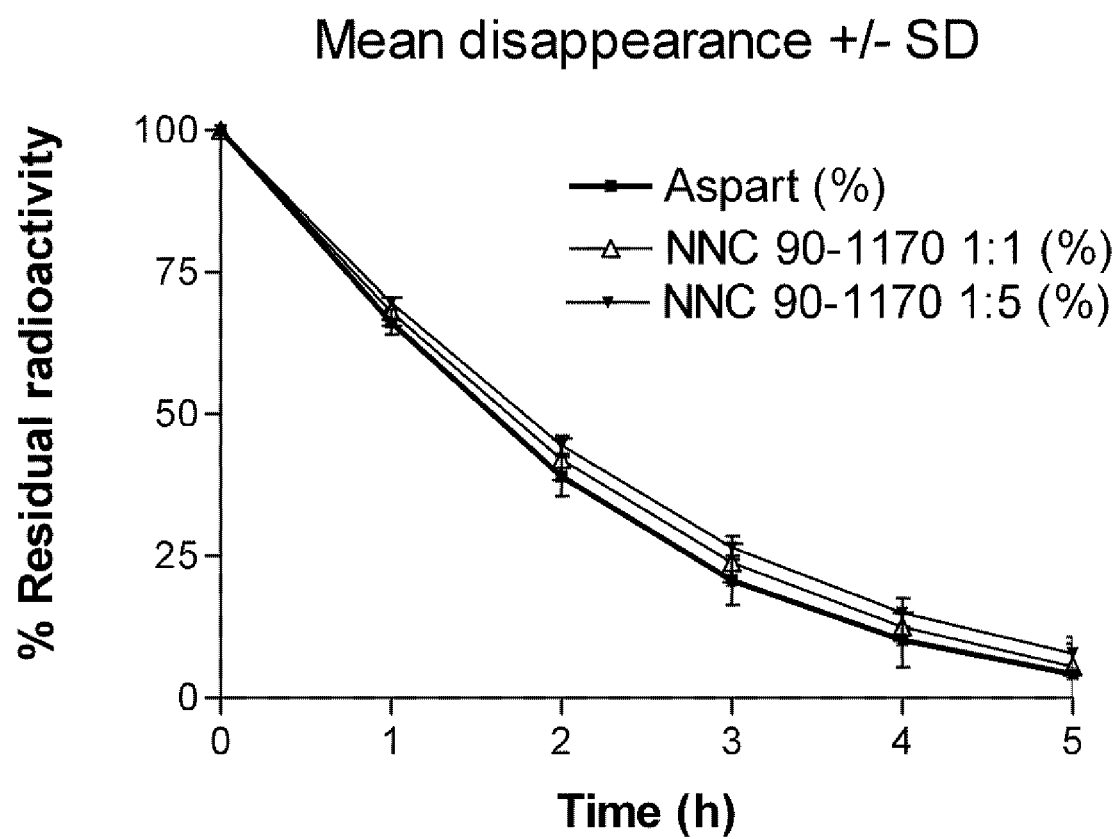
FIG. 1. Average disappearance curves showing the disappearance of radiolabeled insulin aspart.

One object of the present invention is to provide a soluble pharmaceutical composition for parenteral administration, which comprises an insulinotropic peptide, a meal related insulin peptide, a pharmaceutically acceptable preservative and optionally an isotonicity agent. In one embodiment of the invention, pH of said pharmaceutical composition or a reconstituted solution of said pharmaceutical composition is from about pH 7.0 to about pH 9.0. In another embodiment of the invention, pH of said pharmaceutical composition or a reconstituted solution of said pharmaceutical composition is from about pH 7.0 to about pH 8.0.

Another object of the invention is to provide a method for the treatment of hyperglycemia comprising parenteral administration of an effective amount of a soluble pharmaceutical composition comprising an insulinotropic peptide, a meal-related insulin peptide, a pharmaceutically acceptable preservative and optionally an isotonicity agent.

DEFINITIONS

The following is a detailed definition of the terms used in the specification.

The term "effective amount" as used herein means a dosage which is sufficient in order for the treatment of the patient to be effective compared with no treatment.

The term "medicament" as used herein means a pharmaceutical composition suitable for administration of the pharmaceutically active compounds to a patient.

The term "pharmaceutical composition" as used herein means a product comprising an active compound or a salt thereof together with pharmaceutical excipients such as buffer, preservative and tonicity modifier, said pharmaceutical composition being useful for treating, preventing or reducing the severity of a disease or disorder by administration of said pharmaceutical composition to a person. Thus a pharmaceutical composition is also known in the art as a pharmaceutical formulation.

The term "soluble pharmaceutical composition" as used herein means an insulinotropic peptide which is substantially soluble, and a meal-related insulin peptide which is substantially soluble in the combined composition. Thus, a predissolved soluble pharmaceutical composition will be substantially soluble, and a soluble pharmaceutical composition which is to be reconstituted will be substantially soluble once it has been dissolved in the prescribed reconstitution liquid. It is to be understood that pH of a pharmaceutical composition which is to be reconstituted is the pH value which is measured on the reconstituted composition produced by reconstitution in the prescribed reconstitution liquid at room temperature.

The term "pharmaceutically acceptable" as used herein means suited for normal pharmaceutical applications, i.e. giving rise to no adverse events in patients etc.

The term "buffer" as used herein refers to a chemical compound in a pharmaceutical composition that reduces the tendency of pH of the composition to change over time as would otherwise occur due to chemical reactions. Buffers include chemicals such as sodium phosphate, TRIS, glycine and sodium citrate.

The term "preservative" as used herein refers to a chemical compound which is added to a pharmaceutical composition to prevent or delay microbial activity (growth and metabolism). Examples of pharmaceutically acceptable preservatives are phenol, m-cresol and a mixture of phenol and m-cresol.

The term "isotonicity agent" as used refers to a chemical compound in a pharmaceutical composition that serves to modify the osmotic pressure of the pharmaceutical composition so that the osmotic pressure becomes closer to that of human plasma. Isotonicity agents include NaCl, glycerol, mannitol etc.

The term "stabilizer" as used herein refers to chemicals added to peptide containing pharmaceutical compositions in order to stabilize the peptide, i.e. to increase the shelf life and/or in-ude time of such compositions. Examples of stabilizers used in pharmaceutical formulations are L-glycine, L-histidine, arginine, polyethylene glycol, and carboxymethylcellulose.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term "prevention of a disease" as used herein is defined as the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders.

The term "insulin peptide" as used herein means a peptide which is either human insulin or a chemically modified human insulin, such as an analog or a derivative thereof.

The term "human insulin" as used herein means the human hormone whose structure and properties are well known. Human insulin has two polypeptide chains that are connected by disulphide bridges between cysteine residues, namely the A-chain and the B-chain. The A-chain is a 21 amino acid peptide and the B-chain is a 30 amino acid peptide, the two chains being connected by three disulphide bridges: one between the cysteines in position 6 and 11 of the A-chain, the second between the cysteine in position 7 of the A-chain and the cysteine in position 7 of the B-chain, and the third between the cysteine in position 20 of the A-chain and the cysteine in position 19 of the B-chain.

The term "analogue" as used herein referring to a peptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide.

The term "derivative" as used herein in relation to a parent peptide means a chemically modified parent protein or an analogue thereof, wherein at least one substituent is not present in the parent protein or an analogue thereof, i.e. a parent protein which has been covalently modified. Typical modifications are amides, carbohydrates, alkyl groups, acyl groups, esters, PEGylations and the like. Examples of derivatives of human insulin are threonine methyl ester$^{B30}$ human insulin and N$^{\epsilon B29}$-tetradecanoyl des(B30) human insulin.

The term "meal-related insulin peptide" as used herein means an insulin peptide which has a time-action of less than 8 hours in standard models of diabetes. Preferably, the meal-related human insulin has a time-action of less than about 5 hours. Preferably, the meal-related insulin has a time-action in the range from 0 hours to about 4 hours. Preferably, the meal-related insulin has a time-action similar to that observed for commercial pharmaceutical compositions of Actrapid®, Novolog®, and Humalog®. The term about in relation to the time-action of insulins means + or −30 minutes.

The term "GLP-1 compound" as used herein means GLP-1(7-37) (SEQ ID NO. 1), insulinotropic analogue thereof and insulinotropic derivatives thereof. Non-limiting examples of GLP-1 analogues are GLP-1(7-36) amide, Arg$^{34}$-GLP-1(7-37), Gly$^8$-GLP-1(7-37), Val$^8$-GLP-1(7-36)-amide and Val$^8$Asp$^{22}$-GLP-1(7-37). Non-limiting examples of GLP-1 derivatives are desamino-His$^7$, Arg$^{26}$, Lys$^{34}$(N$^\epsilon$-(γ-Glu(N$^\alpha$-hexadecanoyl)))-GLP-1(7-37), desamino-His$^7$, Arg$^{26}$, Lys$^{34}$ (N$^\epsilon$-octanoyl)-GLP-1(7-37), Arg$^{26,34}$, Lys$^{33}$(N$^\epsilon$-(ω-carboxypentadecanoyl))-GLP-1(7-38), Arg$^{26,34}$, Lys$^{36}$(N$^\epsilon$-(γ-Glu(N$^\alpha$-hexadecanoyl)))-GLP-1(7-36) and Arg$^{34}$, Lys$^{26}$(N$^\epsilon$-(γ-Glu(N$^\alpha$-hexadecanoyl)))-GLP-1(7-37).

The term "stable GLP-1 compound" as used herein means a chemically modified GLP-1(7-37), i.e. an analogue or a derivative which exhibits an in vivo plasma elimination half-life of at least 10 hours in man, as determined by the following method. The method for determination of plasma elimination half-life of a peptide in man is: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e.g. Predose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43(51): A143, 2000. Derived pharmacokinetic parameteres are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

The term "dipeptidyl aminopeptidase IV protected GLP-1 compound" as used herein means a GLP-1 compound which is more resistant to the plasma peptidase dipeptidyl aminopeptidase IV (DPP-IV) than the native GLP-1 agonist, GLP-1(7-37). Resistance of a GLP-1 compound towards degradation by dipeptidyl aminopeptidase IV is determined by the following degradation assay:

Aliquots of the GLP-1 compound (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the peptide degradation products are separated and quantified using HPLC analysis. One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a GLP-1 compound by dipeptidyl aminopeptidase IV is estimated at incubation times which result in less than 10% of the GLP-1 compound being hydrolysed.

The term "insulinotropic" as used herein referring to a peptide or a compound means the ability to stimulate secretion of insulin in response to an increased plasma glucose level. Insulinotropic peptides and compounds are agonists of the GLP-1 receptor. The insulinotropic property of a compound may be determined by in vitro or in vivo assays known in the art. The following in vitro assay may be used to determine the insulinotropic nature of a compound such as a peptide. Preferably insulinotropic compounds exhibit an EC$_{50}$ value in below assay of less than 5 nM, even more preferably EC50 values less than 500 pM.

Baby hamster kidney (BHK) cells expressing the cloned human GLP-1 receptor (BHK 467-12A) are grown in DMEM media with the addition of 100 IU/mL penicillin, 100 μL/mL streptomycin, 10% foetal calf serum and 1 mg/mL Geneticin G-418 (Life Technologies). Plasma membranes are prepared by homogenization in buffer (10 mM Tris-HCl, 30 mM NaCl and 1 mM dithiothreitol, pH 7.4, containing, in addition, 5 mg/mL leupeptin (Sigma), 5 mg/L pepstatin (Sigma), 100 mg/L bacitracin (Sigma), and 16 mg/L aprotinin (Calbiochem-Novabiochem, La Jolla, Calif.)). The homogenate was centrifuged on top of a layer of 41% W7v sucrose. The white band between the two layers was diluted in buffer and centrifuged. Plasma membranes were stored at −80° C. until used.

The functional receptor assay is carried out by measuring cAMP as a response to stimulation by the insulinotropic peptide or insulinotropic compound. Incubations are carried out in 96-well microtiter plates in a total volume of 140 mL and with the following final concentrations: 50 mM Tris-HCl, 1 mM EGTA, 1.5 mM MgSO$_4$, 1.7 mM ATP, 20 mM GTP, 2 mM 3-isobutyl-1-methylxanthine (IBMX), 0.01% w/v Tween-20, pH 7.4. Compounds are dissolved and diluted in buffer. GTP is freshly prepared for each experiment: 2.5 μg of membrane is added to each well and the mixture is incubated for 90 min at room temperature in the dark with shaking. The reaction is stopped by the addition of 25 mL 0.5 M HCl. Formed cAMP is measured by a scintillation proximity assay (RPA 542, Amersham, UK). A dose-response curves is plotted for the compound and the EC$_{50}$ value is calculated using GraphPad Prism software.

The term "prodrug of an insulinotropic compound" as used herein means a chemically modified compound which following administration to the patient is converted to an insulinotropic compound. Such prodrugs are typically amino acid extended versions or esters of an insulinotropic compound.

The term "exendin-4 compound" as used herein is defined as exendin-4(1-39) (SEQ ID NO. 2), insulinotropic fragments thereof, insulinotropic analogs thereof and insulinotropic derivatives thereof. Insulinotropic fragments of exendin-4 are insulinotropic peptides for which the entire sequence can be found in the sequence of exendin-4 (SEQ ID NO. 2) and where at least one terminal amino acid has been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogs of exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. An example of an insulinotropic analog of exendin-4(1-39) is Ser$^2$Asp$^3$-exendin-4(1-39) wherein the amino acid residues in position 2 and 3 have been replaced with serine and aspartic acid, respectively (this particular analog also being known in the art as exendin-3). Insulinotropic derivatives of exendin-4(1-39) and analogs thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups, esters and lipophilic substituents. An example of an insulinotropic derivatives of exendin-4(1-39) and analogs thereof is Tyr$^{31}$-exendin-4(1-31)-amide.

The term "stable exendin-4 compound" as used herein means a chemically modified exendin-4(1-39), i.e. an analogue or a derivative which exhibits an in vivo plasma elimination half-life of at least 10 hours in man, as determined by the method described under the definition of "stable GLP-1 compound".

The term "dipeptidyl aminopeptidase IV protected exendin-4 compound" as used herein means an exendin-4 compound which is more resistant towards the plasma peptidase dipeptidyl aminopeptidase IV (DPP-IV) than exendin-4 (SEQ ID NO. 2), as determined by the assay described under the definition of dipeptidyl aminopeptidase IV protected GLP-1 compound.

The term "isoelectric point" as used herein means the pH value where the overall net charge of a macromolecule such as a peptide is zero. In peptides there may be several charged groups, and at the isoelectric point the sum of all these charges is zero. At a pH above the isoelectric point the overall net charge of the peptide will be negative, whereas at pH values below the isoelectric point the overall net charge of the peptide will be positive.

The term "reconstituted" as used herein referring to a pharmaceutical composition means an aqueous composition which has been formed by the addition of water to a solid material comprising the active pharmaceutical ingredient. Pharmaceutical compositions for reconstitution are applied where a liquid composition with acceptable shelf-life cannot be produced. An example of a reconstituted pharmaceutical composition is the solution which results when adding water to a freeze dried composition. The solution is often for parenteral administration and thus water for injection is typically used for reconstituting the solid material.

The term "about" as used herein in relation to the concentration of a peptide in a pharmaceutical composition means plus or minus 10%. Hence, the concentration "about 5 mg/mL insulin" means a concentration of 4.5 mg/mL insulin to 5.5 mg/mL insulin.

DESCRIPTION OF THE INVENTION

In one aspect the invention relates to a pharmaceutical composition for parenteral administration, which comprises an insulinotropic peptide, a meal-related insulin peptide, a pharmaceutically acceptable preservative and optionally an isotonicity agent.

In embodiment of the invention the pH of said pharmaceutical composition or a reconstituted solution of said pharmaceutical composition is from pH 7.0 to pH 9.0.

In embodiment of the invention the pH of said pharmaceutical composition or a reconstituted solution of said pharmaceutical composition is from pH 7.0 to pH 8.0.

In another embodiment of the invention the composition is a solution. In another embodiment of the invention the pharmaceutical composition is a solid. In another embodiment of the invention the pharmaceutical composition is to be reconstituted with an aqueous solution such as a buffer or water for injection.

In another embodiment of the invention the pharmaceutical composition is suitable for administration by injection or infusion. In another embodiment of the invention the pharmaceutical composition is suitable for subcutaneous administration. In another embodiment of the invention the pharmaceutical composition is suitable for intramuscular administration. In another embodiment of the invention the pharmaceutical composition is suitable for intravenous administration.

In a further embodiment the present invention relates to a pharmaceutical composition wherein the meal-related insulin peptide has a time action of less than 4 hours.

In another aspect the present invention relates to a pharmaceutical composition wherein said insulin peptide is human insulin, an analogue of human insulin, a derivative of human insulin or a derivative of a human insulin analogue.

In one embodiment of the invention said insulin peptide is human insulin.

In a further aspect the present invention relates to a pharmaceutical composition wherein said insulin peptide is a human insulin analogue. In one embodiment of the invention said human insulin analogue is Asp$^{B28}$-human insulin. In another embodiment of the invention said human insulin analogue is Lys$^{B28}$,Pro$^{B29}$-human insulin. In another embodiment of the invention said human insulin analogue is Lys$^{B3}$, Glu$^{B29}$-human insulin. In another embodiment of the invention said human insulin analogue is des(B30) human insulin. In another embodiment of the invention said insulin peptide is a derivative of a human insulin analogue.

In another embodiment of the invention the concentration of said meal-related insulin peptide in said pharmaceutical composition is in the range from about 1.6 mg/mL to about 5.6 mg/mL, or from about 2.6 mg/mL to about 4.6 mg/mL, or from about 3.2 mg/mL to about 4.0 mg/mL.

In another embodiment of the invention the concentration of said meal-related insulin peptide in said pharmaceutical composition is in the range from about 1 mg/mL to about 10 mg/mL, or from about 2.5 mg/mL to about 8.75 mg/mL, or from about 3.5 mg/mL to about 8.75 mg/mL, or from about 5 mg/mL to about 8.75 mg/mL.

In another embodiment of the invention the pharmaceutical composition comprises two different insulin peptides.

In another aspect the present invention relates to a pharmaceutical composition wherein said insulinotropic peptide is GLP-1(7-37) (SEQ ID NO. 1), a GLP-1(7-37) analogue, a derivative of GLP-1(7-37), or a derivative of a GLP-1(7-37) analogue. In another embodiment of the invention said GLP-1(7-37) analogue is selected from the group consisting of Arg$^{34}$-GLP-1(7-37), Gly$^8$-GLP-1(7-36)-amide, Gly$^8$-GLP-1 (7-37), Val$^8$-GLP-1(7-36)-amide, Val$^8$-GLP-1(7-37), Val$^8$Asp$^{22}$-GLP-1(7-36)-amide, Val$^8$Asp$^{22}$-GLP-1(7-37), Val$^8$-Glu$^{22}$-GLP-1(7-36)-amide, Val$^8$Glu$^{22}$-GLP-1(7-37), Val⁸Lys²²-GLP-1(7-36)-amide, Val⁸Lys²²-GLP-1(7-37), Val⁸Arg²²-GLP-1(7-36)-amide, Val⁸Arg²²-GLP-1(7-37), Val⁸His²²-GLP-1(7-36)-amide, Val⁸His²²-GLP-1(7-37), Val⁸Trp¹⁹Glu²²-GLP-1(7-37), Val⁸Glu²²Val²⁵-GLP-1(7-37), Val⁸Tyr¹⁶Glu²²-GLP-1(7-37), Val⁸Trp¹⁶Glu²²-GLP-1(7-37), Val⁸Leu¹⁶Glu²²-GLP-1(7-37), Val⁸Tyr¹⁸Glu²²-GLP-1(7-37), Val⁸Glu²²His³⁷-GLP-1(7-37), Val⁸Glu²²Ile³³-GLP-1(7-37), Val⁸Trp¹⁶Glu²²Val²⁵Ile³³-GLP-1(7-37), Val⁸Trp¹⁶Glu²²Ile³³-GLP-1(7-37), Val⁸Glu²²Val²⁵Ile³³-GLP-1(7-37), Val⁸Trp¹⁶Glu²²Val²⁵-GLP-1(7-37), analogues thereof and derivatives of any of these.

In another embodiment of the invention said insulinotropic peptide has a Glu residue in position 22. In another embodiment of the invention said insulinotropic peptide has a L-histidine residue in position 8. In another embodiment of the invention said insulinotropic peptide has a Val residue in position 8. In another embodiment of the invention said derivative of a GLP-1(7-37) analogue is GLP-1(7-36)-amide.

In another aspect the present invention relates to a pharmaceutical composition wherein said insulinotropic peptide is a derivative of GLP-1(7-37) or a derivative of a GLP-1(7-37) analogue having a lysine residue, such as one lysine, wherein a lipophilic substituent optionally via a spacer is attached to the epsilon amino group of said lysine. In one embodiment of the invention said lipophilic substituent has from 8 to 40 carbon atoms, preferably from 8 to 24, eg 12-18. In another embodiment of the invention said spacer is present and is selected from an amino acid, eg. beta-Ala, L-Glu, aminobutyroyl. In another embodiment of the invention said insulinotropic peptide is a dipeptidyl aminopeptidase IV protected GLP-1 compound. In another embodiment of the invention said insulinotropic peptide is a plasma stable GLP-1 compound. In another embodiment of the invention said derivative of a GLP-1(7-37) analogue is Arg³⁴, Lys²⁶(Nᵋ-(γ-Glu(Nᵅ-hexadecanoyl)))-GLP-1(7-37). In another embodiment of the invention said insulinotropic peptide has from 27 to 43 amino acid residues, preferable from 28 to 38 amino acid residues, even more preferable from 30 to 34 amino acid residues.

In another embodiment of the invention the concentration of said insulinotropic peptide in said pharmaceutical composition is from about 1 mg/mL to about 25 mg/mL, from about 2 mg/mL to about 15 mg/mL, from about 5 mg/mL to about 12 mg/mL, or from about 8 mg/mL to about 11 mg/mL. In another embodiment of the invention the concentration of said insulinotropic peptide in said pharmaceutical composition is from about 5 mg/mL to about 7.5 mg/mL.

In another aspect the present invention relates to a pharmaceutical composition wherein said insulinotropic peptide is exendin-4 (SEQ ID NO. 2), an exendin-4 analogue, a derivative of exendin-4, or a derivative of an exendin-4 analogue. In one embodiment of the invention said insulinotropic peptide is exendin-4 (SEQ ID NO. 2). In another embodiment of the invention said exendin-4 analogue is exendin-3 or ZP-10 (HGEGTFTSDLSKQMEEEAVR-LFIEWLKNGGPSSGAPPSKKKKKK-NH2, SEQ ID NO. 3).

In another embodiment of the invention said derivative of an exendin-4 analogue is an acylated exendin-4 analogue or a pegylated exendin-4 analogue. In another embodiment of the invention said insulinotropic peptide is a derivative of exendin-4 or a derivative of an exendin-4 analogue having a lysine residue, such as one lysine, wherein a lipophilic substituent optionally via a spacer is attached to the epsilon amino group of said lysine. In another embodiment of the invention said lipophilic substituent has from 8 to 40 carbon atoms, preferably from 8 to 24, eg 12-18. In another embodiment of the invention said spacer is present and is selected from an amino acid, eg. beta-Ala, L-Glu, aminobutyroyl. In another embodiment of the invention said insulinotropic peptide is a dipeptidyl aminopeptidase IV protected exendin-4 compound. In another embodiment of the invention said insulinotropic peptide is a plasma stable exendin-4 compound. In another embodiment of the invention said insulinotropic peptide has from 30 to 48 amino acid residues, from 33 to 45 amino acid residues, preferable from 35 to 43 amino acid residues, even more preferable from 37 to 41 amino acid residues. In another embodiment of the invention the concentration of said insulinotropic peptide in said pharmaceutical composition is from about 5 µg/mL to about 10 mg/mL, from about 5 µg/mL to about 5 mg/mL, from about 0.1 mg/mL to about 3 mg/mL, or from about 0.2 mg/mL to about 1 mg/mL.

In another aspect the present invention relates to a pharmaceutical composition wherein the isoelectric point of said insulinotropic peptide is from 3.0 to 7.0, from 4.0 to 6.0, preferable from 4.2 to 5.5, even more preferable from 4.3 to 5.2.

In one aspect the present invention relates to a pharmaceutical composition which further comprises zinc. In one embodiment of the invention the molar ratio of zinc to insulin peptide is from ⅙ to ½ mole/mole, preferable from 3/12 to 5/12 mole/mole.

In another aspect the present invention relates to a pharmaceutical composition, wherein said meal-related insulin peptide is human insulin and said insulinotropic peptide is Arg³⁴, Lys²⁶(Nᵋ-(γ-Glu(Nᵅ-hexadecanoyl)))-GLP-1(7-37). In one embodiment of the invention the concentration of Arg³⁴, Lys²⁶(Nᵋ-(γ-Glu(Nᵅ-hexadecanoyl)))-GLP-1(7-37) is in the range from about 1 mg/mL to about 25 mg/mL and the concentration of human insulin is in the range from about 3.2 mg/mL to about 4.0 mg/mL. In another embodiment of the invention the concentration of Arg³⁴, Lys²⁶(Nᵋ-(γ-Glu(Nᵅ-hexadecanoyl)))-GLP-1(7-37) is in the range from about 5 mg/mL to about 15 mg/mL and the concentration of human insulin is in the range from about 3.2 mg/mL to about 4.0 mg/mL.

In another aspect the present invention relates to a pharmaceutical composition, wherein said insulin peptide is Asp$^{B28}$-human insulin and said insulinotropic peptide is Arg³⁴, Lys²⁶(Nᵋ-(γ-Glu(Nᵅ-hexadecanoyl)))-GLP-1(7-37). In one embodiment of the invention the concentration of Arg³⁴, Lys²⁶(Nᵋ-(γ-Glu(Nᵅ-hexadecanoyl)))-GLP-1(7-37) is in the range from about 1 mg/mL to about 25 mg/mL and the concentration of Asp$^{B28}$-human insulin is in the range from about 3.2 mg/mL to about 4.0 mg/mL. In another embodiment of the invention the concentration of Arg³⁴, Lys²⁶(Nᵋ-(γ-Glu(Nᵅ-hexadecanoyl)))-GLP-1(7-37) is in the range from about 5 mg/mL to about 15 mg/mL and the concentration of Asp$^{B28}$-human insulin is in the range from about 3.2 mg/mL to about 4.0 mg/mL. In another embodiment of the invention the concentration of Arg³⁴, Lys²⁶(Nᵋ-(γ-Glu(Nᵅ-hexadecanoyl)))-GLP-1(7-37) is in the range from about 1 mg/mL to about 25 mg/mL and the concentration of Asp$^{B28}$-human insulin is in the range from about 3.4 mg/mL to about 3.8 mg/mL. In another embodiment of the invention the concentration of Arg³⁴, Lys²⁶(Nᵋ-(γ-Glu(Nᵅ-hexadecanoyl)))-GLP-1(7-37) is in the range from about 5 mg/mL to about 15 mg/mL and the concentration of Asp$^{B28}$-human insulin is in the range from about 3.4 mg/mL to about 3.8 mg/mL.

In another aspect the present invention relates to a pharmaceutical composition, wherein said insulin peptide is Lys$^{B3}$, Glu$^{B29}$-human insulin and said insulinotropic peptide is ZP-10 (HGEGTFTSDLSKQMEEEAVR-LFIEWLKNGGPSSGAPPSKKKKKK-NH2, SEQ ID NO.

3). In one embodiment of the invention the concentration of Lys$^{B3}$,Glu$^{B29}$-human insulin is in the range from about 3.2 mg/mL to about 4.0 mg/mL. In another embodiment of the invention the concentration of ZP-10 is in the range from about 0.1 mg/mL to about 3 mg/mL.

In another embodiment of the present invention the preservative is phenol, m-cresol or a mixture thereof.

In another aspect of the present invention the pharmaceutical composition comprises a buffer.

In one embodiment of the invention said buffer is phosphate, TRIS, HEPES, glycine, N-glycylglycine, citrate or mixtures thereof.

In another aspect of the present invention the pharmaceutical composition comprises an isotonicity agent. In one embodiment the isotonicity agent is not a salt. In another embodiment the isotonicity agent is selected from mannitol, sorbitol, glycerol, propylene glycol or a mixture thereof.

In another aspect the present invention relates to a soluble pharmaceutical composition for parenteral administration, which comprises an insulinotropic peptide, a meal-related insulin peptide, a pharmaceutically acceptable preservative, a stabiliser and optionally an isotonicity agent. In one embodiment of the invention said stabiliser is selected from the group consisting of L-histidine, imidazole and L-arginine. In another embodiment of the invention said stabiliser is a polyethylene glycol.

In another aspect the present invention relates to a soluble pharmaceutical composition which comprises an insulinotropic peptide, a meal-related insulin peptide, a pharmaceutically acceptable preservative, a surfactant and optionally an isotonicity agent.

In one embodiment the surfactant is a poloxamer.

In another embodiment the surfactant is a poloxamer 188.

In another embodiment the surfactant is selected from the group consisting of poloxamer 407, poloxamer 124, poloxamer 181, poloxamer 182, poloxamer 237, poloxamer 331 and poloxamer 338.

In another embodiment the surfactant is a polysorbate 20 (Tween-20).

In another embodiment the concentration of said surfactant is from about 5 mg/L to about 3000 mg/L.

In another embodiment the concentration of said surfactant is from about 10 mg/L to about 500 mg/L.

In another embodiment the concentration of said surfactant is from about 20 mg/L to about 300 mg/L.

In another embodiment the concentration of said surfactant is from about 50 mg/L to about 200 mg/L.

In another embodiment the pharmaceutical composition comprises two different surfactants.

In another embodiment the pharmaceutical composition comprises poloxamer 188 and polysorbate 20 (Tween-20).

In another embodiment of the invention the surfactant is selected from a detergent, ethoxylated castor oil, polyglycolyzed glycerides, acetylated monoglycerides, sorbitan fatty acid esters, poloxamers, such as poloxamer 188 and poloxamer 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives- (e.g. sodium taurodihydrofusidate etc.), long-chain fatty acids and salts thereof C6-C12 (eg. oleic acid and caprylic acid), acylcarnitines and derivatives, N$^\alpha$-acylated derivatives of lysine, arginine or histidine, or side-chain acylated derivatives of lysine or arginine, N$^\alpha$-acylated derivatives of dipeptides comprising any combination of lysine, arginine or histidine and a neutral or acidic amino acid, N$^\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention. In a further embodiment of the invention the surfactant is a polysorbate, such as polysorbate-20. In a further embodiment of the invention the pharmaceutical composition comprises a surfactant in a concentration from about 1 ppm to about 500 ppm, preferably from about 10 ppm to about 120 ppm.

In another aspect the present invention relates to a method for treatment of hyperglycemia comprising parenteral administration of an effective amount of a pharmaceutical composition, which comprises an insulinotropic peptide, a meal-related insulin peptide, a pharmaceutically acceptable preservative, and optionally an isotonicity agent.

In another aspect the present invention relates to a method for treatment of binge eating or bulimia comprising parenteral administration of an effective amount of a pharmaceutical composition, which comprises an insulinotropic peptide, a meal-related insulin peptide, a pharmaceutically acceptable preservative, and optionally an isotonicity agent.

In another aspect the present invention relates to a method for treatment or prevention of type 2 diabetes, impaired glucose tolerance, type 1 diabetes, obesity, hypertension, syndrome X, dyslipidemia, cognitive disorders, atteroschlerosis, myocardial infarction, coronary heart disease and other cardiovascular disorders, stroke, inflammatory bowel syndrome, dyspepsia and gastric ulcers comprising parenteral administration of an effective amount of a pharmaceutical composition, which comprises an insulinotropic peptide, a meal-related insulin peptide, a pharmaceutically acceptable preservative, and optionally an isotonicity agent.

In another aspect the present invention relates to a method for delaying or preventing disease progression in type 2 diabetes comprising parenteral administration of an effective amount of a pharmaceutical composition, which comprises an insulinotropic peptide, a meal-related insulin peptide, a pharmaceutically acceptable preservative, and optionally an isotonicity agent.

In another aspect the present invention relates to a method for decreasing food intake, decreasing β-cell apoptosis, increasing β-cell function and β-cell mass, and/or for restoring glucose sensitivity to β-cells comprising parenteral administration of an effective amount of a pharmaceutical composition, which comprises an insulinotropic peptide, a meal-related insulin peptide, a pharmaceutically acceptable preservative, and optionally an isotonicity agent.

When the pharmaceutical compositions according to the present invention are administered by injection, e.g. via a pen or a syringe, it is typically administered 3 times per day, preferably before meals. It is preferred that each administration comprises less than about 500 µL, or less than about 200 µL since larger injection volumes are unpleasant for the patient. When the pharmaceutical compositions according to the present invention are administered by a pump, it is typically administered continuously or discontinuously via at least 10 administrations or more per day. In one embodiment of the invention the method of treatment comprises administration of an effective amount of the pharmaceutical composition which is from about 30 µL/day to about 600 µL/day, such as from about 60 µL/day to about 360 µL/day. In another embodiment of the invention the method comprises a pharmaceutical composition for administration by subcutaneous injection. In another embodiment of the invention the method comprises a pharmaceutical composition for administration by a pump. In another embodiment of the invention the method comprises administration by a pump which delivers a discontinuous amount of said pharmaceutical composition. In another embodiment of the invention the method comprises administration by a pump which delivers a discontinuous amount of said pharmaceutical composition wherein said discontinuous administration of said pharmaceutical composition is by a pulse dosing for a period of time which is less than the period between pulses.

In another aspect the present invention relates to the use of an insulinotropic peptide and a meal-related insulin peptide for the manufacture of a pharmaceutical composition for parenteral administration, which composition comprises an insulinotropic peptide, a meal-related insulin peptide, a pharmaceutically acceptable preservative, and optionally an isotonicity agent. In one embodiment of the invention the use comprises a pharmaceutical composition for administration by subcutaneous injection. In another embodiment of the invention the use comprises a pharmaceutical composition for administration by a pump. In another embodiment of the invention the use comprises administration by a pump which delivers a discontinuous amount of said pharmaceutical composition. In another embodiment of the invention the use comprises administration by a pump which delivers a discontinuous amount of said pharmaceutical composition wherein said discontinuous administration of said pharmaceutical composition is by a pulse dosing for a period of time which is less than the period between pulses.

In another aspect the present invention relates to the use of an insulin peptide and an insulinotropic peptide for the manufacture of a pharmaceutical composition for the treatment of hyperglycemia by parenteral administration, which composition comprises an insulin peptide, an insulinotropic peptide, a pharmaceutically acceptable buffer, a pharmaceutically acceptable preservative, a surfactant and optionally an isotonicity agent.

EXAMPLES

Example 1

In Vivo Pig Data of Mixtures

Two mixtures of insulin aspart (Asp$^{B28}$-human insulin) and Liraglutide (Arg$^{34}$Lys$^{26}$N$^{\epsilon}$(γ-Glu(N$^{\alpha}$-hexadecanoyl))GLP-1 (7-37)), with insulin aspart labelled in TyrA14 with $^{125}$I, were prepared for subcutaneous administration to pigs. The study design was simultaneous measuring of insulin aspart disappearance from the injection site by external gamma counting, and monitoring of Liraglutide plasma concentration time course for up to 72 hours.

Aspart Formulation (Reference)

600 µM Aspart (with tracer), 300 µM Zn(Ac)$_2$, pH 7.4, 30 mM phenol, 1.6% glycerol.

Mix Aspart:Liraglutide Formulation, 1:1

600 µM Aspart (with tracer), 600 µM Liraglutide, 300 µM Zn(Ac)$_2$, pH 7.4, 30 mM phenol, 1.6% glycerol.

Mix Aspart:Liraglutide Formulation, 1:5

600 µM Aspart (with tracer), 3000 µM Liraglutide, 300 µM Zn(Ac)$_2$, pH 7.4, 30 mM phenol, 1.6% glycerol.

Six normal and healthy pigs (Dansk Landrace, LDY) having a body weight of 80 kg to 100 kg were included in the study. The pigs were each administered 100 µL insulin aspart formulation (reference) at one side of the neck and 100 µL mix aspart/liraglutide formulation at the opposite side. Disappearance courses of radiolabelled insulin aspart were measured at both injection sites in 6 pigs for the insulin aspart reference, and in 3 pigs for each mix 1:1 and 1:5. Simultaneously blood samples were collected over a period of 72 hours to monitor the plasma concentration time course of Liraglutide.

Average Disappearance Curves with Standard Deviations

The average disappearance curves are shown in FIG. 1. The disappearance versus time of insulin aspart from the subcutaneous tissue following administration of the 1:5 mixture was only slightly slower than for both the reference and the 1:1 mixture. The mean (SD) time point for 75%, 50% and 25% of the remaining radioactivity following injection, were calculated, please refer to table 1 below.

TABLE 1

Summary of disappearance study.

|  | Insulin Aspart reference (n = 6) | Mix 1:1 (n = 3) | Mix 1:5 (n = 3) |
|---|---|---|---|
| T75% (h) | 0.75 ± 0.05 | 0.79 ± 0.07 | 0.83 ± 0.03 |
| T50% (h) | 1.60 ± 0.11 | 1.70 ± 0.13 | 1.78 ± 0.05 |
| T25% (h) | 2.79 ± 0.26 | 2.96 ± 0.23 | 3.14 ± 0.18 |

Pharmacokinetics of Liraglutide

Pharmacokinetics were calculated on plasma concentration time data. Based on AUC it was concluded that absorption of liraglutide was independent of the mixture applied, since liraglutide from the 1:5 formulation give rise to a 5-fold increase in AUC, thereby confirming unchanged relative bioavailability of Liraglutide.

Based on above PK parameters, a simulation was performed illustrating co-administration (with Aspart) of 0.2 nmol/kg Liraglutide at mealtimes (breakfast, lunch, and dinner). App. 0.2 nmol/kg of Liraglutide at meal time are providing a satisfying Liraglutide plasma level indicating that 1:1 is the most likely Aspart:Liraglutide ratio.

Figure 2:
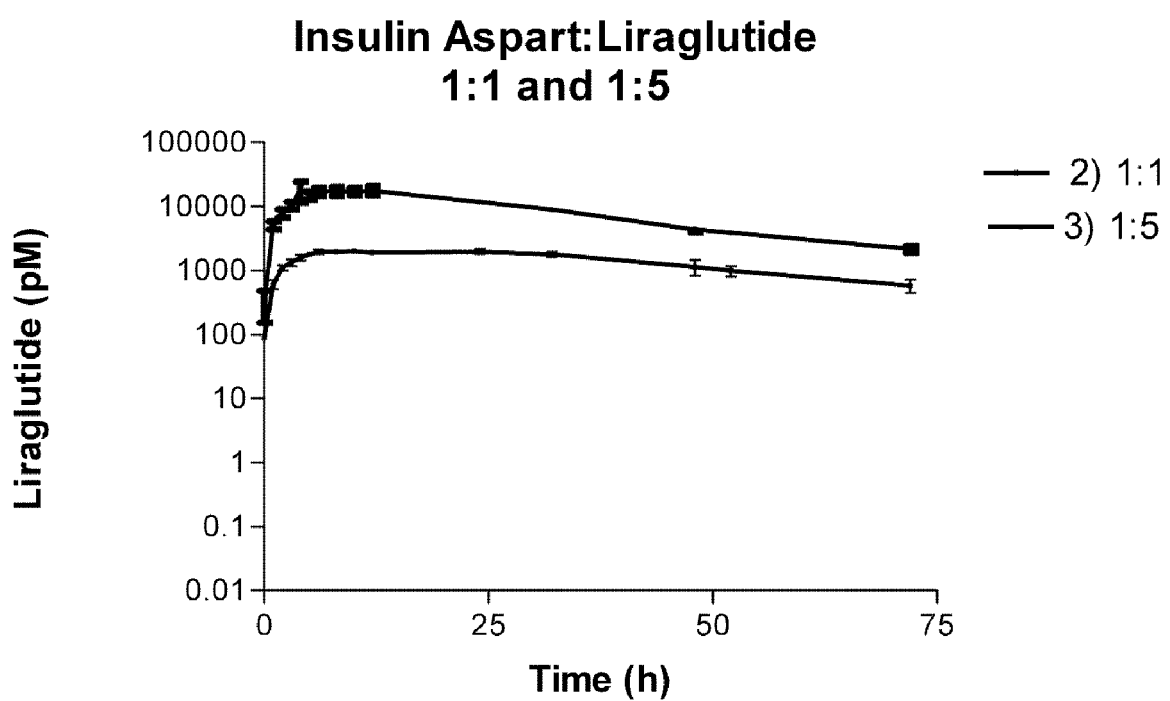
FIG. 2. Plasma levels of liraglutide after subcutaneous injections of the mixtures (logarithmic scale).
Figure 3:
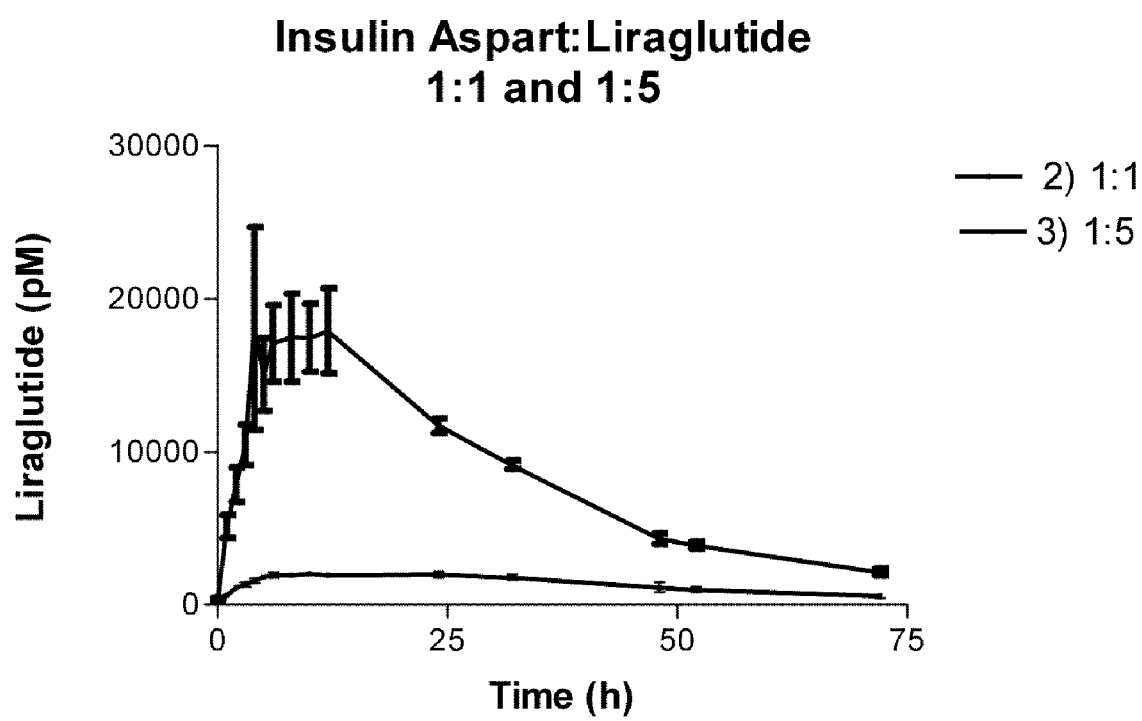
FIG. 3. Plasma levels of liraglutide after subcutaneous injections of the mixtures (linear scale).

FIGS. 2 and 3 show the plasma levels of liraglutide after subcutaneous injections of the mixtures described above.

TABLE 2

| Liraglutide PK parameters n = 3 | | | | |
|---|---|---|---|---|
| $t_{max}$ (hr) | $C_{max}$ (pmol/L) | $t\frac{1}{2}$ (hr) | AUC (hr * pmol/L) | Extr (%) |
| 2) 1:1 | | | | |
| Mean 12.0 | 2180 | 26.2 | 123488 | 18 |
| SD 10.4 | 209 | 5.7 | 34562 | 6 |
| Harmonic Mean 8.0 | 2166 | 25.5 | 117918 | 17 |
| 3) 1:5 | | | | |
| Mean 8.0 | 21187 | 19.2 | 665435 | 9 |
| SD 4.0 | 8751 | 2.8 | 59264 | 3 |
| Harmonic Mean 6.5 | 19230 | 18.9 | 661980 | 8 |

Example 2

Figure 4:
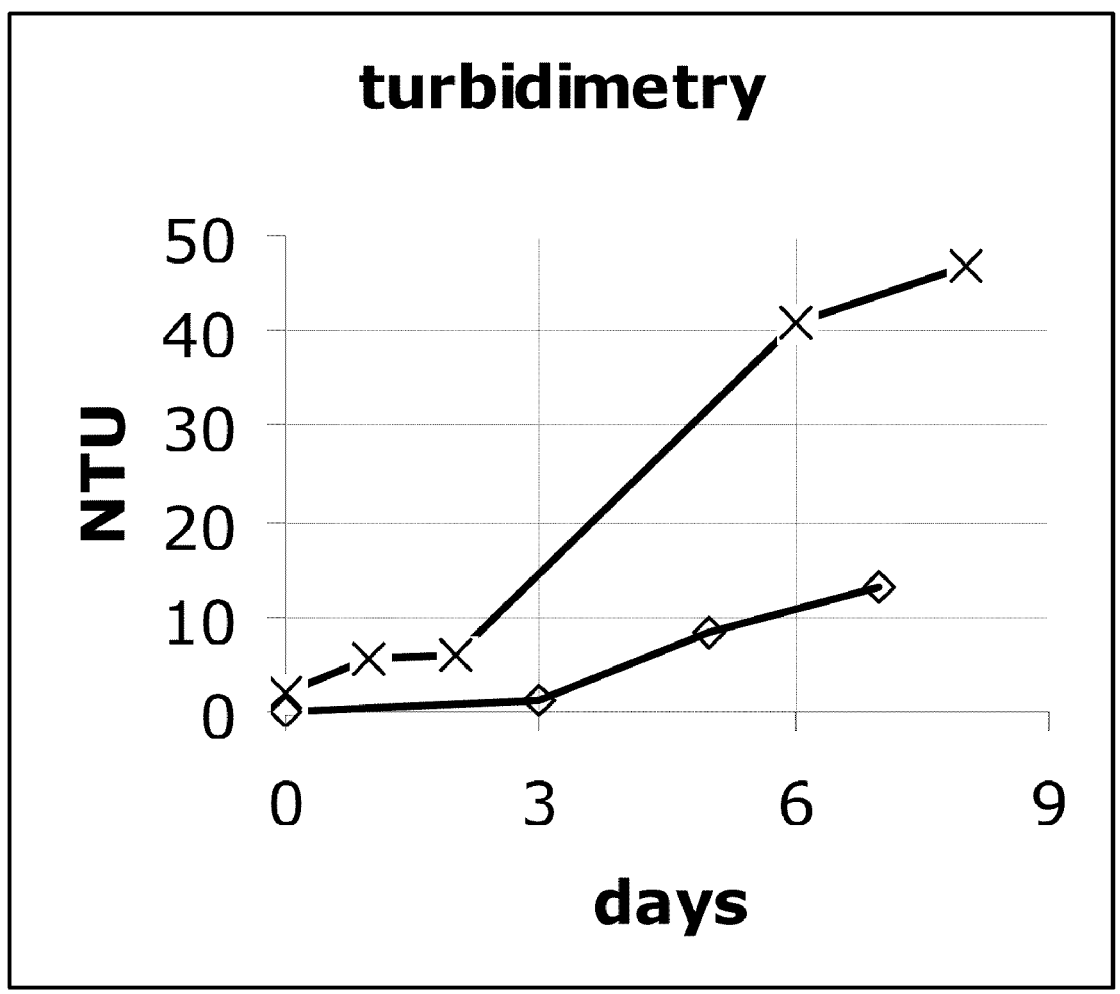
FIG. 4. Turbidimetric measurements of two pharmaceutical compositions containing aspart and liraglutide. Pharmaceutical composition without poloxamer 188 (x) and with poloxamer 188 (◊) (500 ppm).

Two pharmaceutical compositions were prepared according to the description of the present invention. Both pharmaceutical compositions comprised the meal related insulin Asp$^{B28}$-human insulin (aspart) and the insulinotropic peptide Arg$^{34}$, Lys$^{26}$(N$^\epsilon$-(γ-Glu(N$^\alpha$-hexadecanoyl)))-GLP-1(7-37) (liraglutide). In both pharmaceutical compositions aspart concentration is 0.6 mM and liraglutide concentration is 1.2 mM. Furthermore both compositions contained 10 mM NaCl, 8 mM phosphate buffer, 14 mg/ml propylene glycol, 40 mM phenol. Turbidimetric measurements of compositions without poloxamer 188 (x) and with poloxamer 188 (◊) (500 ppm) are shown for 8 and 7 days, respectively (FIG. 4).

Example 3

Figure 5:
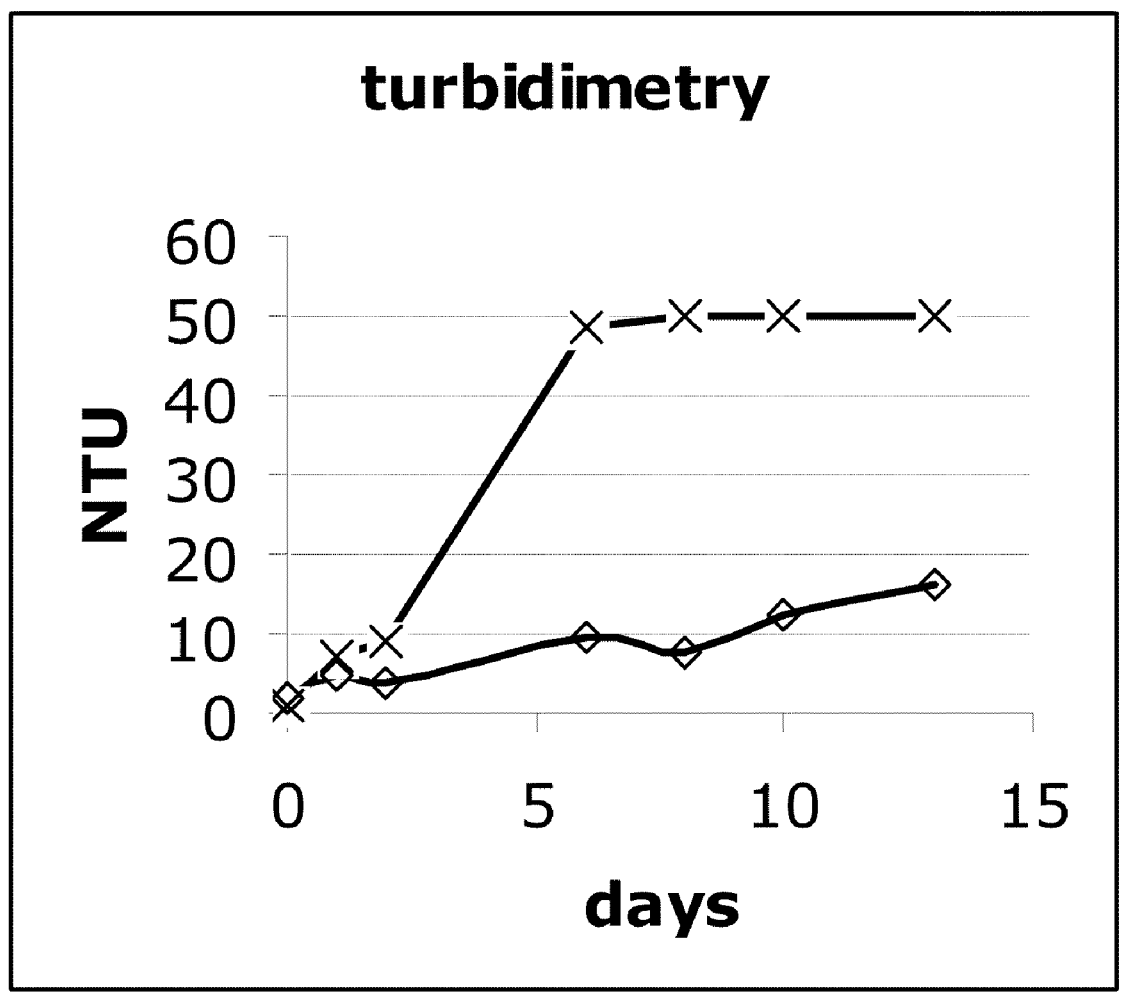
FIG. 5. Turbidimetric measurements of two pharmaceutical compositions containing aspart and liraglutide. Pharmaceutical composition without poloxamer 188 (x) and with poloxamer 188 (◊) (50 ppm).

Two pharmaceutical compositions were prepared according to the description of the present invention. Both pharmaceutical compositions comprised the meal related insulin Asp$^{B28}$-human insulin (aspart) and the insulinotropic peptide Arg$^{34}$, Lys$^{26}$(N$^\epsilon$-(γ-Glu(N$^\alpha$-hexadecanoyl)))-GLP-1(7-37) (liraglutide). In both pharmaceutical compositions aspart concentration is 0.6 mM and liraglutide concentration is 1.2 mM. Furthermore both compositions contained 0.35 mM 5-[6-(5-Cyano-1H-[1,2,3]triazol-4-yl)naphthalen-2-yloxy]pentanoic acid, 10 mM bicine buffer, 14 mg/ml propylene glycol, 40 mM phenol. Turbidimetric measurements of pharmaceutical compositions without poloxamer 188 (x) and with poloxamer 188 (◊) (50 ppm) were performed for 13 days (FIG. 5).

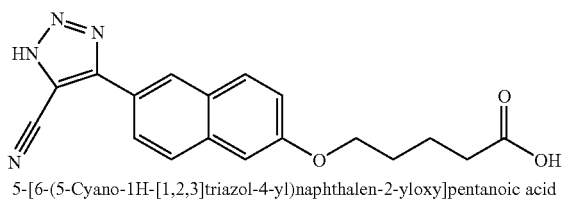

5-[6-(5-Cyano-1H-[1,2,3]triazol-4-yl)naphthalen-2-yloxy]pentanoic acid

Example 4

The following pharmaceutical compositions are prepared
F1. 1.2 mM liraglutide, 14 mg/ml propylene glycol, 40 mM phenol, 3 Zn/hex, aspart 0.6 mM, 8 mM bicine, 50 ppm poloxamer 188, pH 7.7.

F2. 1.2 mM liraglutide, 14 mg/ml propylene glycol, 40 mM phenol, 3 Zn/hex, aspart 0.6 mM, 8 mM bicine, pH 7.7.

Physical stability of the pharmaceutical compositions is evaluated by means of an accelerated stressed test. The stressed test is performed as a rotation test. 50 µL air is added to 5 cartridges (glass vials) of each formulation. The cartridges are rotated with a frequency of 30 rotations per minute for 4 hours daily. The test is stopped after 22 days of rotation. The inspection of the cartridges is followed daily or as required. The turbidity of the formulation is characterized by nephelometric measurement of the turbidity on a HACH Turbidimeter 2100AN. The turbidity measurement of a liquid is specified in "Nephelometric Turbidity Unit" (NTU). Physical instability of the protein is characterised by high turbidity measurements.

The experiments show that the NTU measurements increase much more rapidly in the F2 composition as compared to the NTU trace of the F1 composition.

Example 5

Thioflavin T (ThT) Fibrillation Assay

Principle and Examples

Low physical stability of a peptide may lead to amyloid fibril formation, which is observed as well-ordered, thread-like macromolecular structures in the sample eventually resulting in gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 309, 274-284].

The time course for fibril formation can be described by a sigmoidal curve with the following expression [Nielsen et al. (2001) Biochemistry 40, 6036-6046]:

$$F = f_i + m_i t + \frac{f_f + m_f t}{1 + e^{-[(t-t_0)/\tau]}} \qquad \text{Eq. (1)}$$

Here, F is the ThT fluorescence at the time t. The constant $t_0$ is the time needed to reach 50% of maximum fluorescence. The two important parameters describing fibril formation are the lag-time calculated by $t_0-2\tau$ and the apparent rate constant $k_{app}=1/\tau$.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Sample Preparation

Samples were prepared freshly before each assay. Each sample composition is described in the legends. The pH of the sample was adjusted to the desired value using appropriate amounts of concentrated NaOH and HClO$_4$. Thioflavin T was added to the samples from a stock solution in H$_2$O to a final concentration of 1 µM.

Sample aliquots of 200 µl were placed in a 96 well microtiter plate (Packard OptiPlate™-96, white polystyrene). Usually, eight replica of each sample (corresponding to one test condition) were placed in one column of wells. The plate was sealed with Scotch Pad (Qiagen).

Incubation and Fluorescence Measurement

Incubation at given temperature, shaking and measurement of the ThT fluorescence emission were done in a Fluoroskan Ascent FL fluorescence platereader (Thermo Labsystems). The temperature was adjusted to 37° C. The orbital shaking was adjusted to 960 rpm with an amplitude of 1 mm in all the presented data. Fluorescence measurement was done using excitation through a 444 nm filter and measurement of emission through a 485 nm filter.

Each run was initiated by incubating the plate at the assay temperature for 10 min. The plate was measured every 20 minutes for typically 45 hours. Between each measurement, the plate was shaken and heated as described.

Data Handling

The measurement points were saved in Microsoft Excel format for further processing and curve drawing and fitting was performed using GraphPad Prism. The background emission from ThT in the absence of fibrils was negligible. The data points are typically a mean of eight samples and shown with standard deviation error bars. Only data obtained in the same experiment (i.e. samples on the same plate) are presented in the same graph ensuring a relative measure of fibrillation between experiments.

The data set may be fitted to Eq. (1). However, since full sigmodial curves in this case are not always achieved during the measurement time, the degree of fibrillation is expressed as ThT fluorescence tabulated as the mean of the eight samples and shown with the standard deviation at various time points.

Example 6

Figure 6:
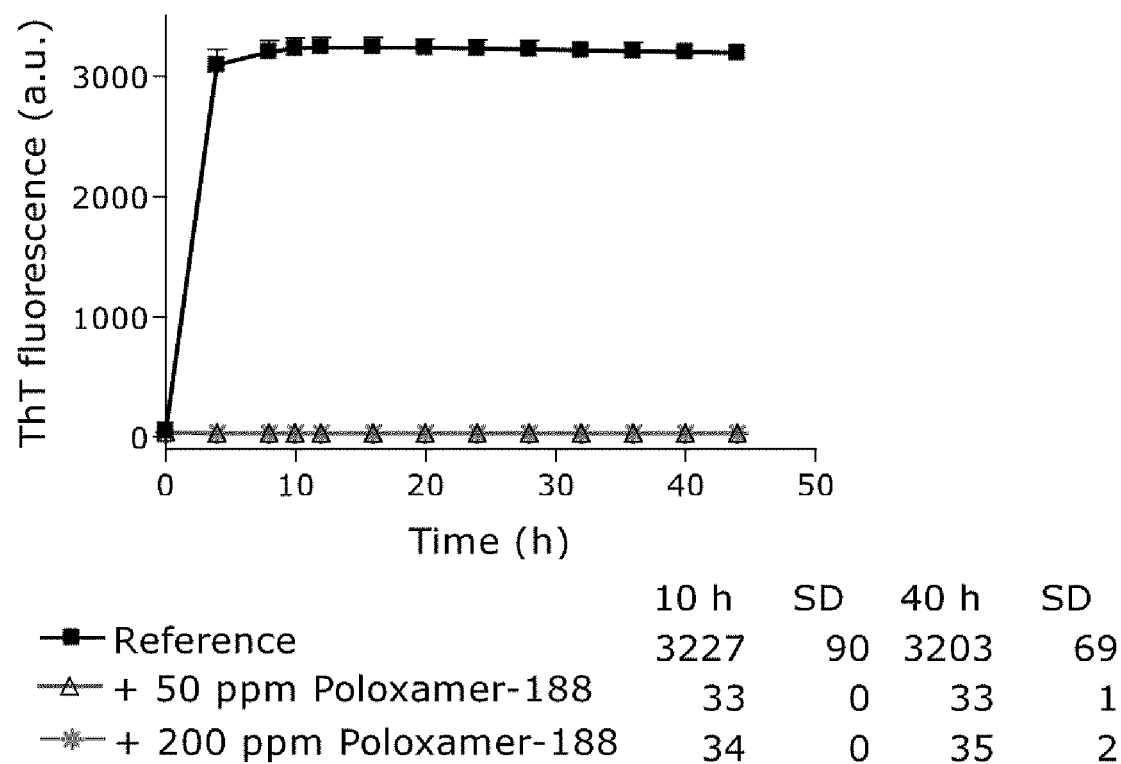
FIG. 6. All samples contain: 0.6 mM insulin aspart, 0.3 mM $Zn(Ac)_2$, 1.2 mM Liraglutide, 14 mg/ml propylene glycol, 40 mM phenol, 10 mM NaCl, pH 7.7. Poloxamer 188 is added to two of the samples.

A formulation of insulin aspart and liraglutide in a 1:2 mix ratio in water adjusted to pH 7.7 is highly physical unstable as seen in FIG. 6. The ThT fluorescence signal increases instantaneously and reaches a plateau before 10 hours of assay time. However, the addition of Poloxamer 188 stabilises this formulation. Both at 50 ppm and 200 ppm Poloxamer 188, the insulin aspart-liraglutide mix formulation does not exhibit any increase in ThT fluorescence above background level, hence these samples are fully physical stable and do not fibrillate.

Example 7

Figure 7:
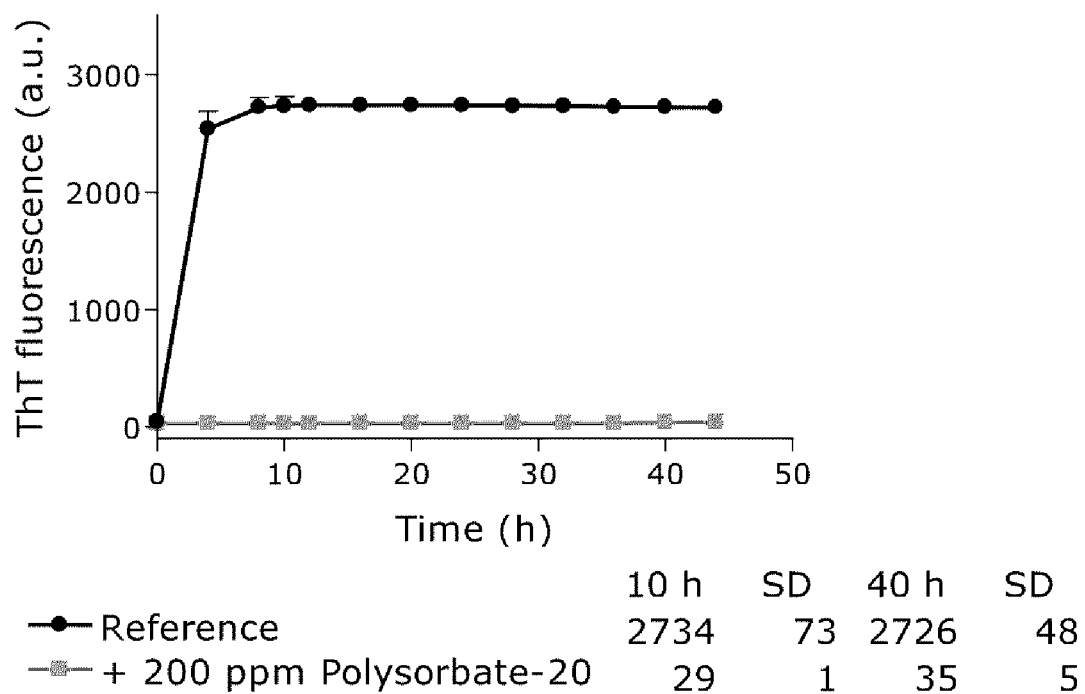
FIG. 7. Both samples contain 0.6 mM insulin aspart, 0.3 mM $Zn(Ac)_2$, 1.2 mM Liraglutide, 40 mM phenol, 14 mg/ml propylene glycol, 10 mM NaCl, pH 7.7. Polysorbate 20 is added to one sample.

Also Polysorbate 20 is capable of stabilising an insulin aspart-liraglutide 1:2 mix formulated in water, see FIG. 7. The presence of 200 ppm Polysorbate 20 fully suppresses fibrillation.

Example 8

Figure 8:
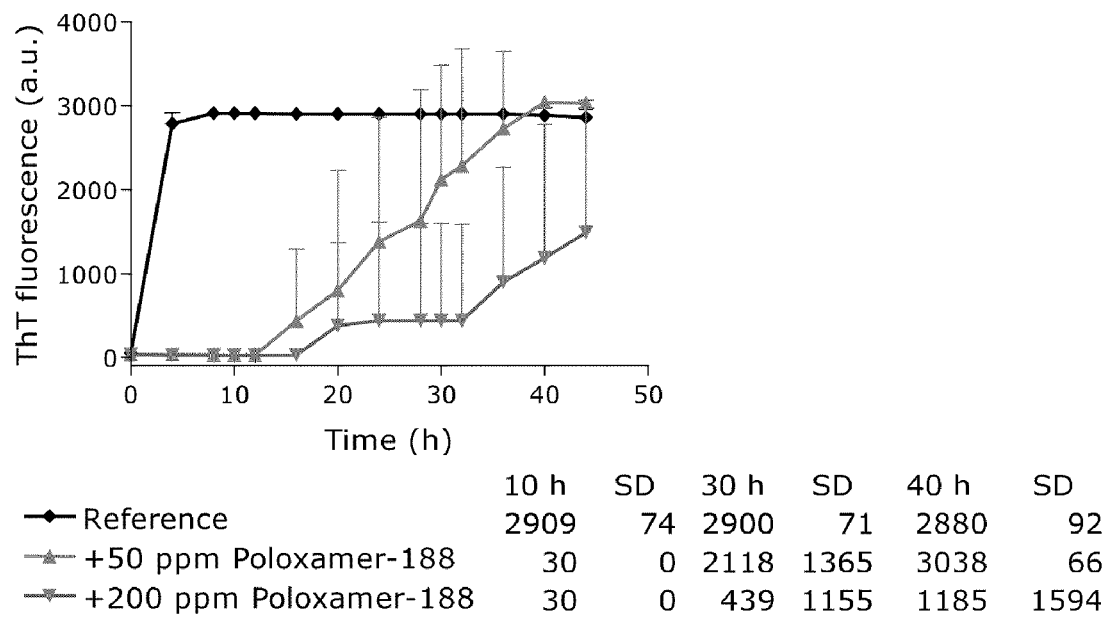
FIG. 8. All samples contain 0.6 mM insulin aspart, 0.3 mM Zn(Ac)$_2$, 1.2 mM Liraglutide, 8 mM sodium phosphate pH 7.7, 40 mM phenol, 14 mg/ml propylene glycol. Poloxamer 188 is added to two samples.

When formulating insulin aspart and liraglutide in a 1:2 mix ratio in sodium phosphate buffer, the sample is highly physically unstable, see FIG. 8. The presence of 50 ppm or 200 ppm Poloxamer 188 prolongs the lag time before on-set of fibrillation: from the instantaneous fibrillation in the absence of Poloxamer 188, it is longer than 15 hours in the presence of either 50 ppm or 200 ppm Poloxamer 188. The sample with the highest Poloxamer 188 concentration exhibits the lowest ThT signal after 40 hours of assay time.

Example 9

Figure 9:
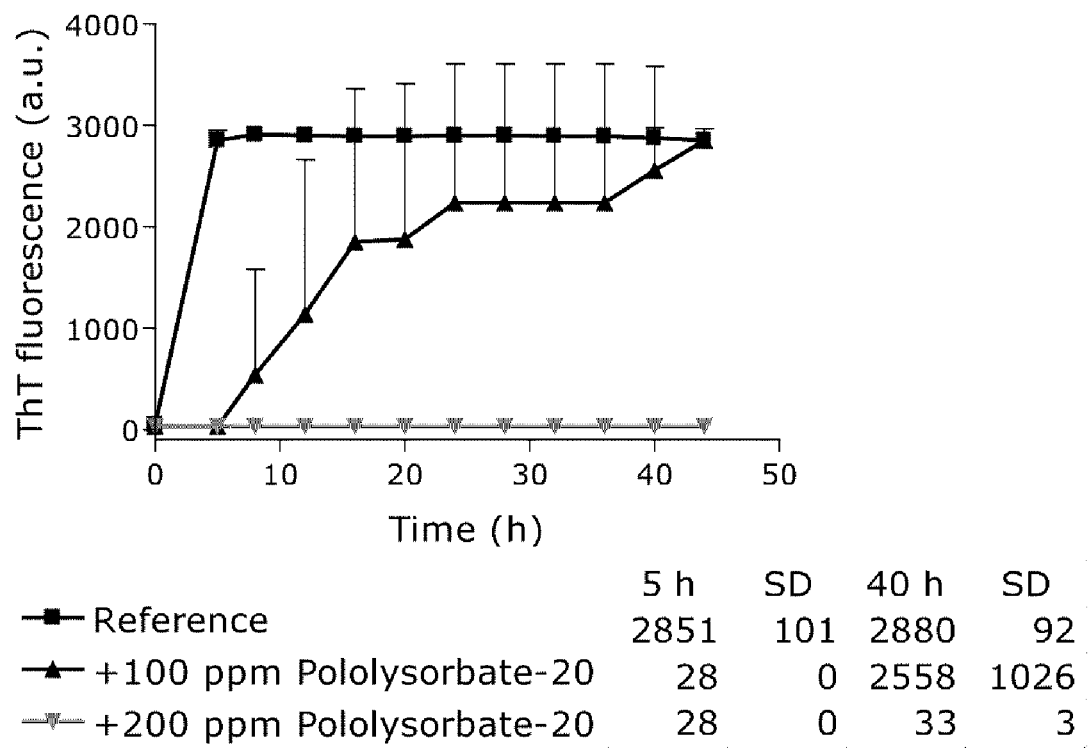
FIG. 9. 0.6 mM insulin aspart, 0.3 mM Zn(Ac)$_2$, 1.2 mM Liraglutide, 8 mM sodium phosphosfate, 40 mM phenol, 14 mg/ml propylene glycol, pH 7.7. Polysorbate 20 is added to two of the samples.

Polysorbate 20 does also stabilise insulin aspart-liraglutide 1:2 mixes formulated in sodium phosphate buffer, see FIG. 9. The presence of 100 ppm Polysorbate 20 increases the lag time to longer than 5 hours compared to the sample without Polysorbate 20. The presence of 200 ppm Polysorbate 20 fully suppresses fibrillation of the sample.

Example 10

Formulations where insulin aspart and liraglutide are mixed in a 1:5 ratio are also highly physical unstable. These formulations are stabilised by the presence of 100 ppm Poloxamer 188 or 200 ppm Polysorbate 20. This is observed as a prolongation of the lag time before on-set of fibrillation in the presence of either Poloxamer 188 or Polysorbate 20 compared with a similar formulation without either Poloxamer 188 or Polysorbate 20.

The invention claimed is:

1. A soluble pharmaceutical composition for parenteral administration, which comprises an insulinotropic peptide, a meal-related insulin peptide, a pharmaceutically acceptable preservative, a surfactant and optionally an isotonicity agent, wherein said insulinotropic peptide is $Arg^{34}$, $Lys^{26}(N^\epsilon\text{-}(\gamma\text{-}Glu(N^\alpha\text{-}hexadecanoyl)))\text{-}GLP\text{-}1(7\text{-}37)$ and wherein said meal-related insulin peptide is $Asp^{B28}$-human insulin.

2. The pharmaceutical composition according to claim 1, wherein the pH of said pharmaceutical composition or a reconstituted solution of said pharmaceutical composition is from about pH 7.0 to about pH 9.0.

3. The pharmaceutical composition according to claim 1, wherein the pH of said pharmaceutical composition or a reconstituted solution of said pharmaceutical composition is from about pH 7.0 to about pH 8.0.

4. The pharmaceutical composition according to claim 1, wherein the composition is a solution.

5. The pharmaceutical composition according to claim 1, wherein the composition is a solid.

6. The pharmaceutical composition according to claim 5, which is to be reconstituted with an aqueous solution such as a buffer or water for injection.

7. The pharmaceutical composition according to claim 1, which is suitable for administration by injection or infusion.

8. The pharmaceutical composition according to claim 1, wherein said meal-related insulin peptide has an onset of action of less than 4 hours.

9. The pharmaceutical composition according to claim 1, wherein the concentration of said meal-related insulin peptide is in the range from about 1.6 mg/mL to about 5.6 mg/mL.

10. The pharmaceutical composition according to claim 1, wherein the concentration of said meal-related insulin peptide is in the range from about 1 mg/mL to about 10 mg/mL.

11. The pharmaceutical composition according to claim 1, wherein the concentration of $Arg^{34}$, $Lys^{26}(N^\epsilon\text{-}(\gamma\text{-}Glu(N^\alpha\text{-}hexadecanoyl)))\text{-}GLP\text{-}1(7\text{-}37)$ is from about 1 mg/mL to about 25 mg/mL.

12. The pharmaceutical composition according to claim 1, wherein the concentration of $Arg^{34}$, $Lys^{26}(N^\epsilon\text{-}(\gamma\text{-}Glu(N^\alpha\text{-}hexadecanoyl)))\text{-}GLP\text{-}1(7\text{-}37)$ is from about 5 μg/mL to about 10 mg/mL.

13. The pharmaceutical composition according to claim 1, wherein the isoelectric point of $Arg^{34}$, $Lys^{26}(N^\epsilon\text{-}(\gamma\text{-}Glu(N^\alpha\text{-}hexadecanoyl)))\text{-}GLP\text{-}1(7\text{-}37)$ is from 3.0 to 7.0.

14. The pharmaceutical composition according to claim 1, said composition further comprising zinc.

15. The pharmaceutical composition according to claim 14, wherein the molar ratio of zinc to insulin peptide is from 1/6 to 1/2 mole/mole.

16. The pharmaceutical composition according to claim 1, wherein the concentration of $Arg^{34}$, $Lys^{26}(N^\epsilon\text{-}(\gamma\text{-}Glu(N^\alpha\text{-}hexadecanoyl)))\text{-}GLP\text{-}1(7\text{-}37)$ is in the range from about 5 mg/mL to about 15 mg/mL and the concentration of $Asp^{B28}$-human insulin is in the range from about 3.2 mg/mL to about 4.0 mg/mL.

17. The pharmaceutical composition according to claim 1, wherein the concentration of $Arg^{34}$, $Lys^{26}(N^\epsilon\text{-}(\gamma\text{-}Glu(N^\alpha\text{-}hexadecanoyl)))\text{-}GLP\text{-}1(7\text{-}37)$ is in the range from about 5 mg/mL to about 15 mg/mL and the concentration of $Asp^{B28}$-human insulin is in the range from about 3.4 mg/mL to about 3.8 mg/mL.

18. The pharmaceutical composition according to claim 1, wherein said preservative is phenol, m-cresol or a mixture thereof.

19. The pharmaceutical composition according to claim 1, wherein said pharmaceutical composition comprises a buffer.

20. The pharmaceutical composition according to claim 19, wherein said buffer is phosphate, TRIS, HEPES, glycine, N-glycylglycine, citrate or a mixture thereof.

21. The pharmaceutical composition according to claim 1, wherein said pharmaceutical composition comprises an isotonicity agent.

22. The pharmaceutical composition according to claim 21, wherein said isotonicity agent is not a salt.

23. The pharmaceutical composition according to claim 22, wherein said isotonicity agent is selected from mannitol, sorbitol, glycerol, propylene glycol or a mixture thereof.

24. The pharmaceutical composition according to claim 1, wherein said composition further comprises a stabiliser.

25. The pharmaceutical composition according to claim 24, wherein said stabiliser is selected from the group consisting of L-histidine, imidazole and L-arginine.

26. The pharmaceutical composition according to claim 24, wherein said stabiliser is a polyethylene glycol.

27. The pharmaceutical composition according to claim 1, wherein said surfactant is a poloxamer.

28. The pharmaceutical composition according to claim 27, wherein said surfactant is a poloxamer 188.

29. The pharmaceutical composition according to claim 27, wherein said surfactant is selected from the group consisting of poloxamer 407, poloxamer 124, poloxamer 181, poloxamer 182, poloxamer 237, poloxamer 331 and poloxamer 338.

30. The pharmaceutical composition according to claim 1, wherein said surfactant is a polysorbate 20 (Tween-20).

31. The pharmaceutical composition according to claim 1, wherein the concentration of said surfactant is from about 5 mg/L to about 3000 mg/L.

32. The pharmaceutical composition according to claim 1, wherein the concentration of said surfactant is from about 10 mg/L to about 500 mg/L.

33. The pharmaceutical composition according to claim 1, wherein the concentration of said surfactant is from about 20 mg/L to about 300 mg/L.

34. The pharmaceutical composition according to claim 1, wherein the concentration of said surfactant is from about 50 mg/L to about 200 mg/L.

35. The pharmaceutical composition according to claim 1, wherein said composition comprises two different surfactants.

36. The pharmaceutical composition according to claim 35, comprising poloxamer 188 and polysorbate 20 (Tween-20).

* * * * *